United States Patent [19]
Rebeller et al.

[11] 4,320,050
[45] Mar. 16, 1982

[54] PROCESS FOR SELECTIVELY EXTRACTING DYESTUFFS CONTAINED IN CYANOPHYCEAE ALGAE, THE SO-EXTRACTED DYESTUFFS AND THEIR USE, PARTICULARLY IN FOODSTUFFS

[75] Inventors: Michel Rebeller, L'Etang la Ville; Pierre Yout, Vienne; Daniel Lonchamp, Tassin la Demi-Lune, all of France

[73] Assignee: Institut Francais du Petrole, Rueil-Malmaison, France

[21] Appl. No.: 137,097

[22] Filed: Apr. 4, 1980

[30] Foreign Application Priority Data

Apr. 6, 1979 [FR] France .................................. 79 09120

[51] Int. Cl.³ ............................................... A23L 1/275
[52] U.S. Cl. .................................. 260/112 R; 426/540; 426/429; 426/431; 426/481; 435/67; 435/946; 8/646; 424/63
[58] Field of Search ................ 426/250, 540, 429, 431, 426/481; 435/67, 946; 260/112 R; 8/53

[56] References Cited

U.S. PATENT DOCUMENTS 2,949,700  8/1960  Kathrein ............................. 435/946
3,108,402  10/1963  Kathrein ............................. 435/946
4,021,303  5/1977  Nakabayashi ....................... 435/946

FOREIGN PATENT DOCUMENTS 5577890  12/1978  Japan .................................. 435/946

Primary Examiner—Jeanette M. Hunter
Attorney, Agent, or Firm—Millen & White

[57] ABSTRACT

Process for extracting dyestuffs and particularly a blue pigment, called phycocyanine, from cyanophyceae algae, particularly of the Spirulina species, comprising contacting said algae with a first aqueous phase containing calcium ions, separating therefrom the mass of algae and contacting it with a second aqueous phase of alkaline character, separating the algae therefrom and extracting phycocyanine from said second aqueous phase by subjecting the same to an ultrafiltration step for concentrating the solution and then to a drying step.

19 Claims, No Drawings

PROCESS FOR SELECTIVELY EXTRACTING DYESTUFFS CONTAINED IN CYANOPHYCEAE ALGAE, THE SO-EXTRACTED DYESTUFFS AND THEIR USE, PARTICULARLY IN FOODSTUFFS

BACKGROUND OF THE INVENTION

The invention concerns a process for selectively extracting dyestuffs contained in cyanophyceae algae, particularly algae of the Spirulina species.

It is known that the so-called "blue" algae (Cyanophyceae) particularly of the Spirulina species, contain a certain number of pigments in various proportions. They consist mainly of:

a green pigment: chlorophyll a, present in a proportion of about 0.1 to 0.15% of the weight of the dry algae;

a blue pigment: phycocyanine, present in a proportion of about 20 to 25% of the weight of the dry algae;

yellow, orange and red pigments: the carotenoids, present in a proportion of about 0.47 to 0.65% of the weight of the dry algae.

The extraction of chlorophyll is not of particular interest in the present case, since this pigment is often present in most of the plants.

On the contrary, the other pigments (blue, orange and red) are of high interest since they are not frequent in the nature. They may advantageously replace the synthetic dyestuffs used, up to now, in human and animal foodstuffs, certain of which are already prohibited or on the way to be prohibited, in view of their actual or suspected toxicity. The blue dyestuff is particularly interesting for use in human foodstuffs, in pharmaceuticals and cosmetics. It is, in fact, a blue protein wherein the phycocyanine pigment is completely bonded to the protein. The protein content of this blue dyestuff is about 65% by weight of the dry substance. Its aminogram is very similar to that of the algae which is used as raw material. This dyestuff is called hereinfter "phycocyanine".

It is already known that phycocyanine may be extracted from Cyanophyceae algae by contacting with an aqueous phase. As a matter of fact, phycocyanine diffuses in water when the algae cells are subjected to a certain lysis. This lysis may be obtained by re-suspending the algae in water, either after drying (for example by lyophilization), or after freezing or crushing of fresh algae.

When dry algae are used, the diffusion of phycocyanine is very slow. When starting from fresh algae, resuspended after freezing or crushing, the lysing of algae cells is generally too high: the diffusion of the pigments is then poorly selective and the separation of the extract from the residual mass of algae is very difficult.

SUMMARY OF THE INVENTION

This invention has the purpose of providing an improved process for extracting phycocyanine from Cyanophyceae algae which does not suffer from the above-mentioned disadvantages: phycocyanine is extracted from fresh algae, without any preliminary treatment such as drying, crushing or freezing; the extraction is also more rapid and more selective. The extraction of phycocyanine may be followed with the extraction of carotenoids, from which it is possible, if so desired, to separate the glycosided xanthophylls, as indicated below.

As a general rule, the process for extracting phycocyanine, according to the invention, comprises the following successive steps:

At first, fresh algae are contacted with an aqueous solution containing calcium ions ($Ca^{2+}$); then the aqueous phase is separated from the mass of algae; then said mass of algae is contacted with an alkaline aqueous phase, finally the aqueous phase is separated from the residual mass of algae. In order to perform the first contact step of the process, the starting material consists generally of fresh algae which can be obtained, for example, directly from culture basins. They are collected, for example, by filtration, optionally followed with a washing with water and/or a vacuum drying. The fresh algae, as used, have in most cases a content of dry material from 10 to 20% by weight. The algae are contacted with an aqueous solution of a calcium salt at a concentration of $Ca^{2+}$ ions in most cases from 0.02 to 0.2 ion-gram per liter (i.e. from 0.8 to 8 g of calcium per liter) and preferably from 0.045 to 0.09 ion-gram per liter (i.e. from 1.8 g to 3.6 g of calcium per liter). The contact is preferably performed by suspending under stirring the algae in said solution. The calcium salt is preferably an inorganic salt, in most cases calcium chloride $CaCl_2$, but it is is also possible to make use of other calcium salts soluble in water, such, for example, as calcium nitrate or nitrite.

The amount of calcium salt solution is preferably from 5 to 30 kg per Kg of algae, estimated in the dry state. The contact is performed at a temperature from 15° to 45° C., preferably from 27° to 35° C. After a contact time of, for example, from 15 minutes to one hour, preferably from 30 to 45 minutes, the biomass is separated from the aqueous phase, for example by filtration. It may be washed with water and dried under vacuum. The algae are then treated with an alkaline aqueous phase having a normality of from 0.001 to 0.1 N, preferably from 0.01 to 0.05 N. It may consist, for example, of a solution of alkaline metal compound of basic pH, particularly a solution of bicarbonates or carbonates of alkaline metals, sodium hydroxide or potassium hydroxide. There can be used, for example, an aqueous solution containing 1 g per liter of sodium bicarbonate. The amount of alkaline solution is preferably from 5 to 30 kg per Kg of algae, estimated in the dry state. The algae may, for example, be suspended in an alkaline solution and the suspension may be homogenized by stirring. The operating temperature ranges, for example, from 15° to 45° C., preferably from 27° to 35° C. In these conditions, the diffusion of the blue pigment (phycocyanine) contained in the algae cells, begins, for example, after 10 or 20 minutes; it is generally optimum after 3 to 4 hours. There is obtained, for example, for the fresh equivalent of 1 kilogram of dry algae treated with 20 kg of alkaline solution, from 7 to 12 grams per liter of blue extract. The aqueous phase with which the phycocyanine was extracted, is separated from the residual algae mass by any convenient means, such for example as decantation and filtration under normal pressure or under reduced pressure. There can be used a filtration adjuvant such, for example, as aluminum sulfate, ferrous sulfate or macromolecular polymers, in a proportion of 1 to 5% by weight with respect to the dry material. The filtration step can be followed with a clarification by centrifugation (e.g. 1500 rpm), in order to separate the last solid particles. The separation may also be performed by centrifugation at high speed. The resultant phycocyanine solution may be stabilized by means of a bacteriostatic product, such for example as salicylic acid, 4-hydroxy benzoic acid or sodium azide.

It may also be sterilized according to conventional techniques. This solution may be used as such for various types of utilization for which it is designed. It may be concentrated by ultrafiltration over a suitable membrane, for example in a ratio from 1 to 10. This operation has the further effect of reducing the content of inorganic ions of the solution and removing certain organic impurities; it is possible to take advantage of it to proceed to a washing by dilution with water. When phycocyanine in a pure state is to be obtained, it may be convenient also to remove from the solution the salts thereof by dialysis or any other equivalent method.

The concentrated phycocyanine solution may be stabilized by addition of a product enabling the formation of a syrup of intermediate moistness (salt, sugar for example). Finally, when it is desired to obtain the blue dyestuff as a dry product (powder), the phycocyanine concentrated solution may be subjected to a drying step, performed for example by lyophilization or spray drying.

After extraction of the phycocyanine, there remains an algae cake deeply colored in green by chlorophyll, of high protein content and containing all the carotenoids and lipids.

The carotenoids are distributed as follows (minimum proportion):

$\beta$-carotene, a yellow pigment, amounting about to 0.23%, zeaxanthine (free xanthophyll), a yellow orange pigment, amounting about to 0.04%, echinenone (free xanthophyll), a red pigment, amounting to about 0.01%, myxoxanthophyll (glycosided xanthophyll), an orange pigment amounting to about 0.17%, and oscillaxanthine (glycosided xanthophyll), a red pigment, amounting to about 0.02%.

This cake may first be used for the preparation of a proteinaceous food or of dyestuff for use in aviculture and pisciculture. For this purpose, it is dried under mild conditions, so as to avoid destruction of the pigments. The operation is conducted, for example, by lyophilization or by spray drying and a powder is thus obtained. This powder may also, according to the invention, be used for extracting carotenoids, according to the process described below.

The dry cake is treated with a liquid phase consisting of an organic solvent or a mixture of organic solvents, capable of extracting carotenoids. There is advantageously used light organic solvents, easy to recover, such, for example, as methanol, either pure or in admixture with a small amount of water, acetone or acetone-methanol mixtures.

After and extraction time of, for example, from 10 to 45 minutes, there is separated, e.g. by filtration and washing:

a liquid solution containing the major portion of the carotenoids (yellow, orange and red pigments), chlorophyll, lipids as well as water and the major part of the inorganic salts present in the starting cake;

a cake containing proteins, as well as chlorophyll, which may be used, after drying, as a protein source for foodstuffs.

If necessary, this cake may be subjected to a further extraction with an organic solvent (in most cases methanol), so as to extract residual amounts of carotenoids.

In the operations performed for extracting carotenoids, such as above-described, it is advantageous, in order to limit the amount of solvent to be used, while performing an extraction as complete and selective as possible, to make use of a multistage counter-current extraction process, such as used in the industry.

From the extraction liquid solution, the solvent can be recovered, for example by evaporation under reduced pressure, advantageously at temperature not exceeding 40° C. The recovered solvent may be used for the extraction of the carotenoids from another portion of algae. It remains a pasty brown residue, of high lipids content, which contains the carotenoids of the starting cake.

This product may be used directly as pigment-containing component in composite foodstuffs designed for animal feeding, particularly in aviculture and pisciculture. In order to facilitate its handling in the grinding and mixing operations performed for producing composite foodstuffs, it is advantageous to evaporate the solvent after addition to the extraction liquid solution of a powdered compound which may be included in the composition of the composite foodstuffs (for example starch or dextrine). The extract fixed on such a carrier becomes solid during the evaporation of the solvent and, accordingly, is more easily used.

Moreover, it is preferable to introduce in the carotenoid residue a small proportion (for example about 100 ppm) of an antioxidant of food grade, such, for example, as tocopherol, butylhydroxytoluene, butylhydroxyanisol, octyl- or dodecyl-gallate or still ascorbyl palmitate. In addition, the carotenoid residue is preferably handled and stored under an inert atmosphere and sheltered from light so as to avoid degradation of the carotenoid structures.

In view of their high coloring power, the glycosided xanthophylls (myxoxanthophyll and oscillaxanthine) are economically of higher interest than $\beta$-carotene. Furthermore, they cannot be found so easily as the latter. Also, it may be interesting, in the process of the invention, to provide for the separation thereof from $\beta$-carotene and free xanthophylls (zeaxanthine and echinenone).

According to the invention, this separation may be performed from the pasty brown residue recovered as above described. This residue is admixed with a polar organic solvent, such as pure acetone; to the obtained liquid solution there is added an agent for the fixation of glycosided xanthophylls. This fixation agent may consist mainly of a foodstuff such for example as starch (from wheat, rice or corn), dextrine, dextrose, wheat meal, sugar (e.g. saccharose), or salt (e.g. sodium chloride), or an inert product, such for example as powdered cellulose, or even powdered alumina or silica (the latter being for example those used as catalyst carriers). After stirring, for example for 10 to 15 minutes, the solvent is evaporated to dryness, preferably at a temperature not in excess of 40° C., under reduced pressure. The solvent may be recovered and used to perform the same operation on a similar residue produced from another algae amount. There is also obtained a brown solid mass which is subjected to an extraction with a non-polar or weakly polar solvent, such as a liquid saturated hydrocarbon (e.g. hexane or pentane), or a mixture of saturated hydrocarbons, or even a petroleum ether. The non-polar or weakly polar compounds are dissolved: lipids, chlorophyll, $\beta$-carotene and free xanthophylls (zeaxanthine and echinenone). By filtration and washing, there is separated:

a liquid solution containing the above compounds in a dissolved state, and a cake strongly red-orange colored by the glycosided xanthophylls.

The liquid solution may be evaporated under reduced pressure and low temperature. The recovered solvent may be used for a new extraction on a mass produced from another portion of algae. The residue, containing lipids, chlorophyll, $\beta$-carotene and free xanthophylls (echinenone and zeaxanthine) may be used as a source of dyestuffs for animal feed, particularly in aviculture and pisciculture. There can be added thereto a small proportion of an anti-oxidant of food grade, such as those mentioned above.

The cake containing the glycosided xanthophylls may be dried under reduced pressure and used as such. It is also possible, if so desired, to recover separately the glycosided xanthophylls by desorption from the carrier (fixation agent) by means of a polar organic solvent such, for example, as acetone, methanol or ethanol. The glycosided xanthophylls are entirely dissolved, leaving the carrier free for use in a subsequent operation with another carotenoid residue. The solution of glycosided xanthophylls may be concentrated by evaporation under reduced pressure at a temperature preferably not in excess of 40° C., advantageously after addition of a small amount of an anti-oxidant of food grade, such as those already mentioned above.

The above-described operations are preferably conducted under an inert atmosphere and in the absence of light, so as to avoid degradation of the carotenoid structures.

The process for extracting phycocyanine pigments and optionally carotenoids has been described with the use, as raw material, of Spirulina algae. In fact, it is applicable to any Cyanophyceae algae since they all contain phycocyanine and carotenoids, but in proportions which vary to a large extent from one species to another.

The following examples illustrate the invention but must not be intended to limit the scope thereof to the particular embodiments described.

EXAMPLE 1

Extraction of phycocyanine from fresh algae 10 kg of fresh algae, not washed (content by weight of dry material: 13%) are suspended into 20 liters of a $CaCl_2$ solution at a concentration of 10 g per liter. (i.e. 0.09 ion-gram $Ca^{2+}/l$). The suspension is homogenized and slowly stirred for 45 minutes at 30° C. The algae are filtered under reduced pressure; they are not washed (dry material content: 13%).

The algae biomass is admixed to 20 liters of water containing 0.5 g/l of sodium bicarbonate and 0.5 g/l of sodium carbonate (pH from 10 to 10.5). The suspension is homogenized, slowly stirred for 2 hours at 30° C., and then allowed to settle for one hour.

By decantation there is recovered the almost-entirely of the aqueous phase; the algae residue is dried under vacuum after addition thereto of a filtration adjuvant consisting of alumina sulfate in a proportion of 5% by weight with respect to the dry material.

There is so obtained 22 liters of a solution of blue dyestuff. It is clarified by centrifugation at 1500 r/mn. The optic density of the solution at 618 nm is 25.

The solution is purified and concentrated by ultrafiltration (membrane separation threshold: 20000 by molecular weight).

The flow rate of the solution is 5 $m^3/h$, the pressure 2 $kg/cm^2$, and the flow rate of the ultrafiltrate is 20 liters/h, as an average.

30 liters of water may be added during the operation in order to carry away a maximum amount of inorganic and organic elements. The ultrafiltration is terminated when the concentrate is brought to a volume of 2.5 liters. Its optic density at 618 nm is 230.

The dyestuff concentrated solution is dried by lyophilization.

There is obtained 275 g of blue powder, i.e. about 210 g per kg of dry algae.

The blue powder is perfectly soluble in water. It has a nitrogen content of 13.3% by weight, a moistness of 4.9% by weight and an ash content of 6% by weight.

There is recovered 5.4 kg of algae residue containing 17% by weight of dry material, it is spray dried. The dry product has a nitrogen content of 10.5% by weight, a moistness of 5.8% by weight, an ash content of 10.2% by weight. The total carotenoid pigments amount to 7.9 g per kg of dry material.

In the described conditions, the added filtration adjuvant being taken into account, the losses are of about 12%.

EXAMPLE 2

Example 1 is repeated except that the drying of the dyestuff concentrated solution is performed by spray drying. The yield of blue powder is not changed. The analysis of this powder gives substantially the same results as those obtained in example 1.

EXAMPLE 3

Extraction of total carotenoids

The algae cake obtained after example 1 above is dried and then crushed for 15 minutes with 5 liters of pure methanol. After filtration under reduced pressure there is obtained:

A liquid solution of a brown-green colour containing lipids, a large portion off chlorophyll and the major portion of the carotenoids contained in the algae, a cake of green colour.

This cake is ground with 1.3 liter of pure methanol and, after filtration, there is obtained:

A green liquid solution which, after addition of fresh methanol, may be used for a first extraction on a second portion of algae, a cake with a very low content of carotenoids which, after drying, may be used as proteinic base in foodstuffs.

From the liquid solution of the first extraction, there is recovered after evaporation under reduced pressure, methanol which is re-used in a subsequent extraction, conducted on another cake of algae from which, for example, the blue pigment has been extracted as in example 1. There is obtained a residue (R) appearing as a brown paste.

EXAMPLE 4

Separation of the glycosided xanthophylls 1 kg of residue (R) is dissolved in 4 liters of pure acetone. 1 kg of powdered cellulose is added thereto. The mixture is stirred for 15 minutes and evaporated to dryness under reduced pressure and at a maximum temperature of 40° C. Acetone is recovered to perform the same operation with a similar residue produced from another algae portion and there is obtained a brown solid mass.

This mass is admixed with 4 liters of petroleum ether (40-65 type) and the resulting mixture is stirred for 15 minutes and filtered under reduced pressure. The cake is washed on the filter with 4 liters of petroleum ether.

The filtrate contains, dissolved in the petroleum ether, lipids, chlorophyll, non polar carotenoids (essentially $\beta$-carotene) and weakly polar carotenoids (essentially echinenone and zeaxanthine). Petroleum ether is recovered by evaporation to dryness under reduced pressure and at a maximum temperature of 40° C.

There is recovered a pasty residue which can be used as a source of coloring material for animal feed.

The cellulose cake, strongly red-orange colored, contains glycosided xanthophylls (essentially myxoxanthophyll and oscillaxanthine). Cellulose is desorbed by means of 3 liters of pure ethanol. The so-regenerated cellulose may be re-used in a subsequent operation with another residue such as R.

The ethanol solution, colored in red by the glycosided xanthophylls, is evaporated under reduced pressure at a temperature of 35° C. There is obtained a brown-red residue consisting of glycosided xanthophylls.

EXAMPLE 5

A new portion of fresh Spirulina algae is subjected to the treatment described in examples 1, 3 and 4, except that, in example 4, cellulose is replaced by powdered alumina, (of the type of the aluminas used as catalyst carrier) and acetone is replaced by methanol.

EXAMPLE 6

Examples 1, 3 and 4 are repeated except that, in example 4, cellulose is replaced by silica (of the type of the silicas used as catalyst carrier).

EXAMPLES 7-14

Examples 1, 3 and 4 are repeated several times except that, in example 4, instead of cellulose, there is used a food product which is:
wheat starch (ex. 7)
rice starch (ex. 8)
corn starch (ex. 9)
dextrine (ex. 10)
dextrose (ex. 11)
wheat meal (ex. 12)
sugar (saccharose) (ex. 13), or
salt (sodium chloride) (ex. 14).

In each of these operations, the obtained cake is washed with petroleum ether and dried; the glycosided xanthophylls are not desorbed.

There is obtained colored products which can be used in animal feed.

What is claimed is:

1. A process for extracting phycocyanine from Cyanophycae algae, comprising the steps of:
   (a) contacting fresh Cyanophycae algae with a first aqueous phase containing calcium ions in an amount of from 0.02 to 0.2 ion-gram per liter, at a temperature, from 15° to 45° C., and under such conditions as to render the phycocyanine in said algae amenable to extraction with an aqueous alkaline solution;
   (b) separating resultant mass of algae from said first aqueous phase;
   (c) contacting said separated mass of algae with a second aqueous phase of an alkaline character comprising at least one compound selected from the group consisting of alkali metal carbonates, alkali metal bicarbonates, sodium hydroxide and potassium hydroxide, the normality thereof being from 0.001 normal to 0.1 normal, at a temperature from 15° to 45° C., for a sufficient time to transfer the phycocyanine from the algae to the second aqueous phase, and
   (d) separating from said second aqueous phase a mass of residual algae, said second aqueous phase containing phycocyanine in a dissolved state.

2. A process according to claim 1, wherein the concentration of calcium ions in said first phase is from 0.045 to 0.09 ion gram per liter.

3. A process according to claim 1 wherein said aqueous phase containing calcium ions is a calcium chloride solution.

4. A process according to claim 1 wherein said aqueous phase containing calcium ions is used in a proportion of 5 to 30 kg per kg of algae, estimated in the dry state.

5. A process according to claim 1 wherein step (a) is performed over a period from 15 minutes to 1 hour.

6. A process according to claim 1 wherein the separation step (b) is performed by filtration.

7. A process according to claim 1 wherein said second aqueous phase of alkaline character is used in a proportion from 5 to 30 kg per kilogram of dry algae.

8. A process according to claim 1 wherein step (d) is followed with a step (e) of concentrating the phycocyanine solution by ultrafiltration.

9. A process according to claim 1 wherein the final phycocyanine solution is subjected to a subsequent drying step, whereby phycocyanine is obtained in a solid state.

10. A process according to claim 9, wherein the drying step is conducted by spray drying.

11. A process according to claim 9, wherein the drying step is performed by lyophilization.

12. A process according to claim 1 comprising additional steps of extracting carotenoid pigments as follows: one step of drying the mass of residual algae from step (d) and at least one step of extracting carotenoids, wherein resultant dried mass is treated with at least one organic solvent selective for carotenoids and there is separated a liquid solution containing the major portion of the carotenoids and a mass of reduced carotenoid content.

13. A process according to claim 12, wherein the light organic solvent used for extracting carotenoids is pure methanol, methanol admixed with a small amount of water, acetone or acetone-methanol mixtures.

14. A process according to claim 12 wherein the liquid solution containing the major portion of the carotenoids is subsequently evaporated to dryness so as to obtain a residue containing said carotenoids.

15. A process according to claim 14, wherein, from the residue containing the carotenoids there are separated two types of carotenoids: on the one hand $\beta$-carotene and free xanthophylls, on the other hand glycosided xanthophylls, by performing the following steps:
contacting said residue with a polar organic solvent, and adding to the resultant liquid solution an agent for the fixation of the glycosided xanthophylls, evaporation of resultant mixture of liquid solution and fixation agent to dryness so as to obtain a solid mass, wherefrom are extracted in particular β-carotene and free xanthophylls by means of a non polar or weakly polar solvent, separation from the liquid solution containing β-carotene and the free xanthophylls, of the solid mass containing the glycosided xanthophylls.

16. A process according to claim 15, wherein the desorption of the glycosided xanthophylls from the solid mass containing them is performed by means of a polar organic solvent, and a solution of glycosided xanthophylls is separated from a solid mass containing said fixation agent.

17. A process according to claim 15, wherein said organic polar solvent is acetone, said agent for the fixation of glycosided xanthophylls is selected from starch, dextrose, wheat meal, sugars, sodium chloride, powdered cellulose, powdered alumina and powdered silica and said non-polar or weakly polar organic solvent is selected from one or more liquid saturated hydrocarbons, and petroleum ether.

18. A process according to claim 16, wherein said polar organic solvent is selected from acetone, methanol and ethanol.

19. A process according to claim 1 wherein the Cyanophyceae algae are of the Spirulina species.

* * * * *